US 7,112,216 B2

(12) United States Patent
Gregorich

(10) Patent No.: US 7,112,216 B2
(45) Date of Patent: Sep. 26, 2006

(54) STENT WITH TAPERED FLEXIBILITY

(75) Inventor: Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 136 days.

(21) Appl. No.: 10/447,377

(22) Filed: May 28, 2003

(65) Prior Publication Data

US 2004/0243216 A1 Dec. 2, 2004

(51) Int. Cl.
*A61F 2/06* (2006.01)
(52) U.S. Cl. .................................................. 623/1.15
(58) Field of Classification Search .............. 623/1.15, 623/1.11, 1.16
See application file for complete search history.

(56) References Cited

U.S. PATENT DOCUMENTS

| | | | |
|---|---|---|---|
| 5,091,205 A | 2/1992 | Fan | 427/2 |
| 5,449,373 A | 9/1995 | Pinchasik et al. | 606/198 |
| 5,697,971 A | 12/1997 | Fischell et al. | 623/1 |
| 5,716,393 A | 2/1998 | Lindenberg et al. | 623/1 |
| 5,728,158 A * | 3/1998 | Lau et al. | 623/23.7 |
| 5,741,333 A | 4/1998 | Frid | 623/12 |
| 5,755,770 A | 5/1998 | Ravenscroft | 623/1 |
| 5,800,514 A | 9/1998 | Nunez et al. | 623/1.51 |
| 5,817,404 A | 10/1998 | Kawakita et al. | 428/209 |
| 5,824,045 A | 10/1998 | Alt | 623/1 |
| 5,824,046 A | 10/1998 | Smith et al. | 623/1 |
| 5,824,059 A * | 10/1998 | Wijay | 623/1.15 |
| 5,827,321 A | 10/1998 | Roubin et al. | 606/195 |
| 5,836,966 A | 11/1998 | St. Germain | 606/198 |
| 5,843,117 A | 12/1998 | Alt et al. | 606/194 |
| 5,855,600 A | 1/1999 | Alt | 623/1 |
| 5,911,732 A | 6/1999 | Hojeibane | 606/194 |
| 5,911,754 A | 6/1999 | Kanesaka et al. | 623/1 |
| 5,925,061 A | 7/1999 | Ogi et al. | 606/198 |
| 5,938,697 A * | 8/1999 | Killion et al. | 623/1.15 |
| 5,948,016 A * | 9/1999 | Jang | 623/1.11 |
| 5,980,553 A | 11/1999 | Gray et al. | 606/198 |
| 6,027,526 A * | 2/2000 | Limon et al. | 623/1.15 |
| 6,106,548 A | 8/2000 | Roubin et al. | 623/1.15 |
| 6,113,627 A * | 9/2000 | Jang | 623/1.5 |
| 6,120,522 A | 9/2000 | Vrba et al. | 606/190 |
| 6,123,721 A | 9/2000 | Jang | 623/1 |
| 6,159,237 A | 12/2000 | Alt et al. | 623/1.11 |
| 6,159,238 A | 12/2000 | Killion et al. | 623/1.11 |
| 6,179,867 B1 * | 1/2001 | Cox | 623/1.15 |
| 6,187,034 B1 | 2/2001 | Frantzen | 623/1.11 |
| 6,200,334 B1 | 3/2001 | Jang | 623/1.11 |
| 6,235,053 B1 | 5/2001 | Jang | 623/1.15 |
| 6,273,910 B1 | 8/2001 | Limon | 623/1.15 |
| 6,355,059 B1 | 3/2002 | Richter et al. | 623/1.17 |
| 6,409,753 B1 | 6/2002 | Brown et al. | 623/1.15 |

(Continued)

FOREIGN PATENT DOCUMENTS

WO 02060344 8/2002

*Primary Examiner*—Corrine McDermott
*Assistant Examiner*—Christopher Prone
(74) *Attorney, Agent, or Firm*—Vidas, Arrett & Steinkraus, P.A.

(57) ABSTRACT

A stent comprises a plurality of serpentine circumferential bands, and a plurality of connector columns. Each connector column is located between two adjacent circumferential bands and comprises one or more connector struts. Each connector strut is connected at one end to one serpentine circumferential band and at another end to another serpentine circumferential band. The number of connectors per connector column decreases from the first free end of the stent to the second free end of the stent.

17 Claims, 9 Drawing Sheets

U.S. PATENT DOCUMENTS

| | | |
|---|---|---|
| 6,416,543 B1 | 7/2002 | Hilaire et al. ............... 623/1.16 |
| 6,461,380 B1 | 10/2002 | Cox ........................... 623/1.17 |
| 6,475,233 B1 | 11/2002 | Trozera ..................... 623/1.15 |
| 6,485,509 B1 | 11/2002 | Killion et al. .............. 623/1.15 |
| 6,503,270 B1 | 1/2003 | Richter et al. ............. 623/1.15 |
| 6,506,201 B1 | 1/2003 | Di Caprio et al. .......... 606/192 |
| 6,511,505 B1 | 1/2003 | Cox et al. .................. 623/1.16 |
| 6,540,774 B1 | 4/2003 | Cox ........................... 623/1.15 |
| 6,569,193 B1 | 5/2003 | Cox et al. .................. 623/1.15 |
| 2001/0027339 A1 | 10/2001 | Boatman et al. ........... 623/1.34 |
| 2001/0041929 A1 | 11/2001 | Oepen ....................... 623/1.15 |
| 2001/0041930 A1 | 11/2001 | Globerman et al. ....... 623/1.16 |
| 2002/0042647 A1 | 4/2002 | Jang ........................... 623/1.15 |
| 2002/0095208 A1 | 7/2002 | Gregorich et al. ......... 623/1.15 |
| 2003/0014101 A1 | 1/2003 | Harrison .................... 623/1.15 |
| 2003/0069633 A1 | 4/2003 | Richter et al. ............. 623/1.22 |
| 2003/0074056 A1 | 4/2003 | Killion et al. .............. 623/1.16 |
| 2003/0144729 A1 | 7/2003 | Bicek et al. ................ 623/1.16 |

\* cited by examiner

STENT WITH TAPERED FLEXIBILITY

BACKGROUND OF THE INVENTION

The use of stents in bodily lumen is well known. A stent is typically delivered in an unexpanded state to a desired location in a bodily lumen via a stent delivery device such as a catheter. Once the stent is at the desired bodily location, it is either expanded with a balloon or other suitable device or allowed to expand by, for example, withdrawing a restraining sheath.

Because a stent and stent delivery system often must be delivered through tortuous anatomy, it would be desirable for the stent delivery system to have a smooth transition of stiffness from the proximal end of the system to the distal end of the system. Less flexibility is desirable at the proximal end of the stent delivery system to allow for adequate pushability of the system. More flexibility is desirable at the distal end to ensure adequate trackability of the system.

There remains a need for stents as well as stent delivery systems including stents that provide for sufficient pushability and adequate trackability in vivo.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent having a first free end and second free end, comprising a plurality of serpentine circumferential bands, and a plurality of connector columns. Each connector column is located between two adjacent circumferential bands and comprises one or more connector struts. Each connector strut is connected at one end to one serpentine circumferential band and at another end to another serpentine circumferential band. The number of connectors per connector column decreases from the first free end of the stent to the second free end of the stent.

Desirably, the number of connectors per connector column decreases uniformly from the first free end of the stent to the second free end of the stent. More desirably, the number of connectors per connector column decreases continuously from the first free end of the stent to the second free end of the stent. Optionally, one of the connector columns will have only a single connector strut.

Each connector strut may optionally be connected at one end to a first location on a serpentine circumferential band and at another end to a second location on an adjacent serpentine circumferential band where the second location is longitudinally and circumferentially offset from the first location.

The invention is also directed to a stent having a first free end and second free end, and comprising a plurality of serpentine circumferential bands, and a plurality of connector columns. Each connector column is located between two adjacent circumferential bands, and comprises one or more connector struts. Each connector strut is connected at one end to one serpentine circumferential band and at another end to another serpentine circumferential band. The length of the connectors in a connector column decreases from the first free end of the stent to the second free end of the stent.

Desirably, the number of connectors per connector column will be constant along the length of the stent. Also desirably, the serpentine circumferential bands will be uniformly spaced from one another along the length of the stent.

Typically, each connector strut will be substantially straight. Each connector strut may be inclined at an angle of inclination relative to the longitudinal axis of the stent, the angle of inclination increasing along the length of the stent.

Each serpentine circumferential band has a first end and a second end and includes a plurality of turns at the first and second ends. The connector struts may optionally extend from a turn on one band to a turn on an adjacent band.

Each connector strut is connected at one end to a first location on a serpentine circumferential band and at another end to a second location on an adjacent serpentine circumferential band. The second location is longitudinally and circumferentially offset from the first location. Desirably, the circumferential offset between turns which are connected to one another via a connector strut increases along the length of the stent.

The invention is also directed to a stent having a first free end and second free end, comprising a plurality of serpentine circumferential bands, and a plurality of connector columns, each connector column located between two adjacent circumferential bands. Each connector column comprises one or more connector struts. Each connector strut is characterized by a width and connected at one end to one serpentine circumferential band and at another end to another serpentine circumferential band.

The width of the connectors in a connector column decreases from the first free end of the stent to the second free end of the stent.

Desirably, the number of connectors per connector column is constant along the length of the stent.

Optionally, the length of the connectors may be constant along the length of the stent.

Typically, each connector strut is substantially straight and inclined at an angle of inclination relative to the longitudinal axis of the stent.

The invention is also directed to a stent having a first free end and second free end, comprising a plurality of serpentine circumferential bands, each serpentine band having a first end and a second end and characterized by a plurality of turns at the first and second ends. The turns are interconnected by band struts having a width, and a plurality of connector columns, each connector column located between two adjacent circumferential bands, each connector column comprising one or more connector struts, each connector strut characterized by a width and connected at one end to one serpentine circumferential band and at another end to another serpentine circumferential band. The width of the band struts decreases from the first free end of the stent to the second free end of the stent.

Desirably, the number of connectors per connector column is constant along the length of the stent.

Optionally, the length of the connectors may be constant along the length of the stent.

Typically, each connector strut is substantially straight and inclined at an angle of inclination relative to the longitudinal axis of the stent.

The invention is also directed to stent having a first free end and second free end, and comprising a plurality of serpentine circumferential bands, each serpentine circumferential band characterized by a thickness, and a plurality of connector columns. Each connector column is located between two adjacent circumferential bands and comprises one or more connector struts. Each connector strut is characterized by a width and connected at one end to one serpentine circumferential band and at another end to another serpentine circumferential band. The thickness of the serpentine circumferential bands decreases from the first free end of the stent to the second free end of the stent.

Desirably, the number of connectors per connector column is constant along the length of the stent.

Optionally, the length of the connectors may be constant along the length of the stent.

Typically, each connector strut is substantially straight and inclined at an angle of inclination relative to the longitudinal axis of the stent.

The invention is also directed to stent having a first free end and second free end, and comprising a plurality of serpentine circumferential bands and a plurality of connector columns. Each connector column is located between two adjacent circumferential bands and comprises one or more connector struts. Each connector strut is connected at one end to one serpentine circumferential band and at another end to another serpentine circumferential band. Desirably, a substantially straight connector strut is inclined at an angle of inclination relative to the longitudinal axis of the stent.

Each connector strut may further include one or more peaks and one or more troughs. Desirably, the length of a connector strut increases in accordance with the number of peaks and struts included in the strut.

The invention is also directed to stent having a first free end and second free end, and comprising a plurality of serpentine circumferential bands, each serpentine circumferential band characterized by having a wavelength, and a plurality of connector columns. Each connector column is located between two adjacent circumferential bands and comprises one or more connector struts. Each connector strut is connected at one end to one serpentine circumferential band and at another end to another serpentine circumferential band. The wavelength of the serpentine circumferential bands increases from the first free end of the stent to the second free end of the stent.

Desirably, each connector strut is substantially straight and is inclined at an angle of inclination relative to the longitudinal axis of the stent.

The invention is also directed to stent having a first free end and second free end, a plurality of serpentine circumferential bands and a plurality of connector columns. Each connector column is located between two adjacent serpentine circumferential bands and comprises one or more connector struts. Each connector strut is connected at one end to one serpentine circumferential band and at another end to another serpentine circumferential band.

Desirably, the number of connectors per connector column decreases from the central portion of the stent to the proximal or distal ends. This results in a stent that has greater flexibility at the proximal and distal ends when compared to a more rigid central portion.

Additional details and/or embodiments of the invention are discussed below.

BRIEF DESCRIPTION OF DRAWINGS

FIGS. 1–4a and 5a show flat patterns of inventive stents.

DETAILED DESCRIPTION OF THE INVENTION

Figure 1:
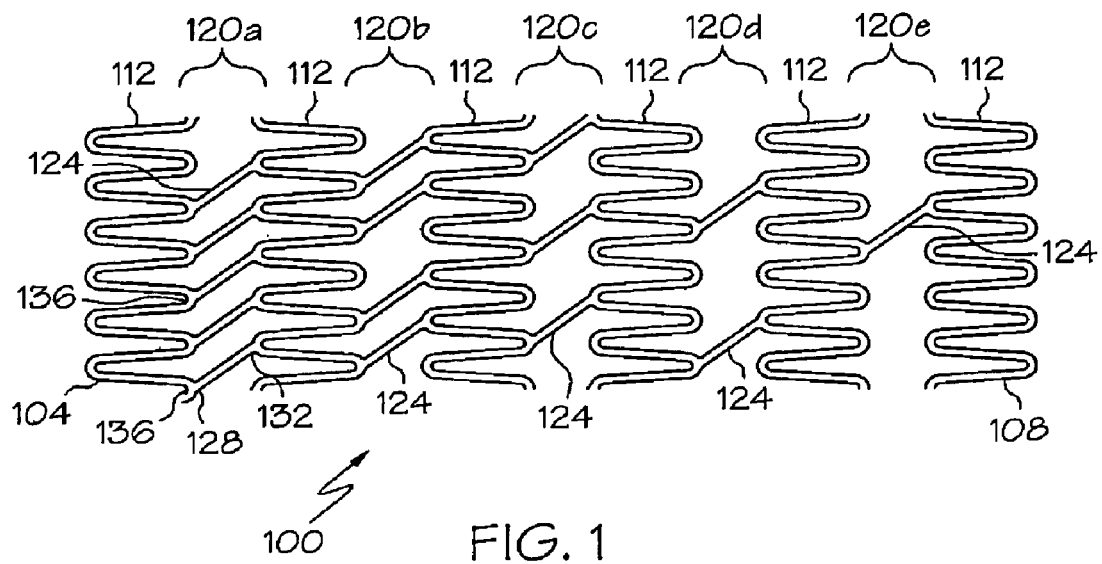

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a stent such as that shown generally at 100 in FIG. 1, having a first free end 104 and a second free end 108, comprising a plurality of serpentine circumferential bands 112, and a plurality of connector columns 120a–e. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. As shown in FIG. 1, the number of connectors per connector column decreases from the first free end of the stent to the second free end of the stent.

Desirably, as shown in FIG. 1, the number of connectors per connector column decreases uniformly from the first free end of the stent to the second free end of the stent. The term 'decrease uniformly' when used in this context refers to the difference between the number of connector struts in adjacent connector columns being constant for every pair of adjacent connector columns. A stent having 3 connector columns in which the first connector column has 6 connector struts, the second connector column has 4 connector struts and the third connector column has 2 connector struts is an example of a uniform decrease in the number of connector struts.

Figure 13:
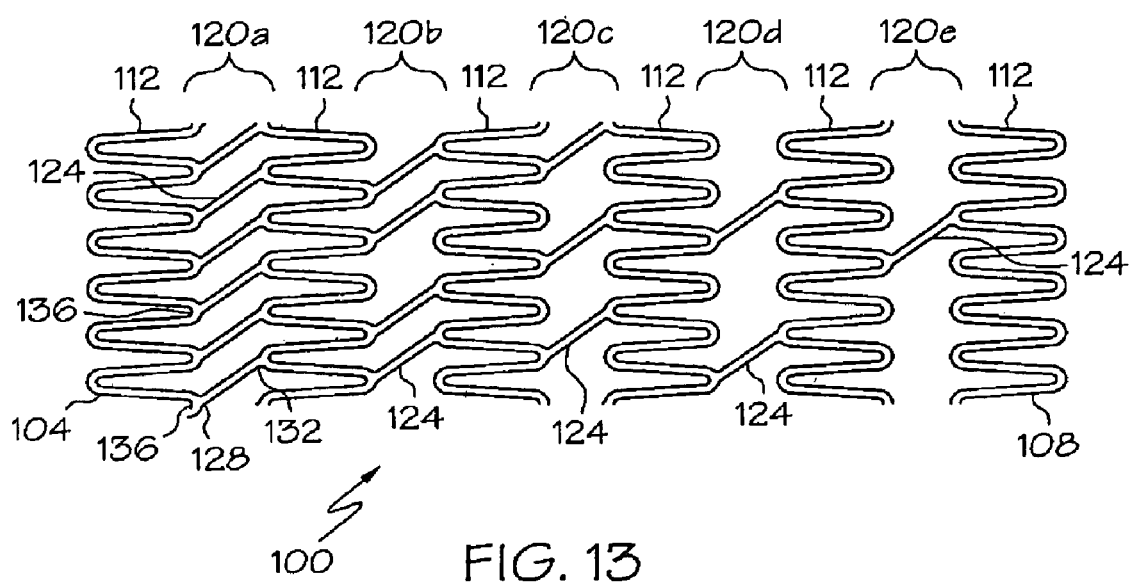
FIG. 13 shows another embodiment of a flat pattern of an inventive stent.

Optionally, the number of connector struts per column may decrease continuously, such as shown in the embodiment depicted in FIG. 13. The term 'decrease continuously' is intended to convey that no two connector columns have the same number of connectors. The invention also contemplates embodiments in which the number of connectors decreases from one end of the stent to the other, but not continuously, as, for example, would be the case if the third connector column 120c of the stent of FIG. 13 were modified to have the same number of connector struts as the second connector column 120b.

In the embodiment of FIG. 13, there is a one to one correspondence between the number of connecting struts 124 and peaks 136 on the first serpentine circumferential band at the proximal end of the stent and a only a single connector strut at the distal end of the stent.

The decrease in the number of connector struts per connector column results in a stent having an increasing flexibility from the proximal end to the distal end of the stent when mounted on a catheter. It is noted that if the stent is reversed, the opposite flexibility gradient results.

As shown in FIG. 1, each connector strut is connected at one end to a first location on a serpentine circumferential band and at another end to a second location on an adjacent serpentine circumferential band where the second location is longitudinally and circumferentially offset from the first location.

Figure 2:
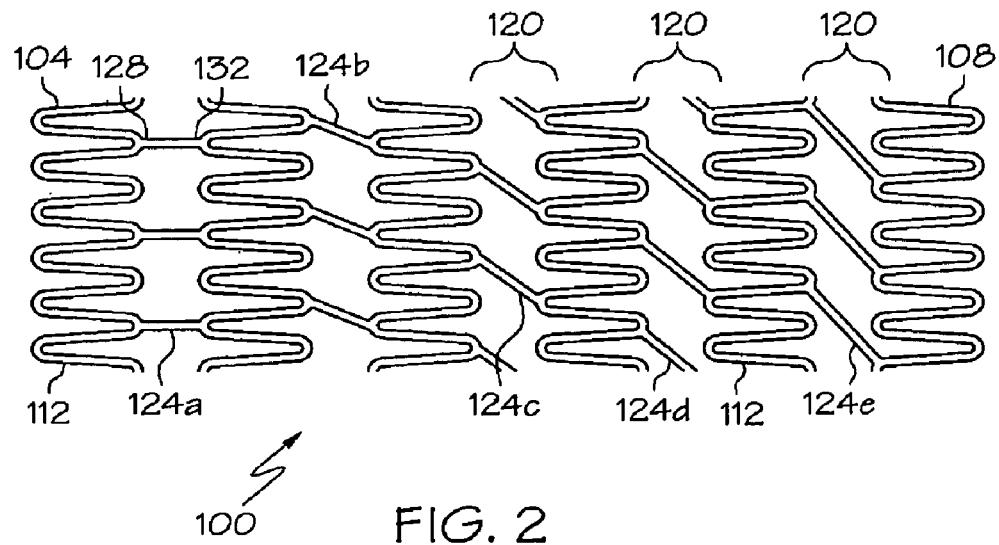

The invention is also directed to a stent shown, generally at 100 in FIG. 2, having a first free end 104 and a second free end 108 and comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. As shown in FIG. 2, the length of the connector struts in a connector column decreases from the first free end of the stent to the second free end of the stent.

Desirably, as shown in FIG. 2, the number of connectors per connector column will be constant along the length of the stent. Also desirably, as shown in FIG. 2, the serpentine circumferential bands will be uniformly spaced from one another along the length of the stent.

Typically, each connector strut will be substantially straight. Each connector strut may be inclined at an angle of inclination relative to the longitudinal axis of the stent, with the angle of inclination increasing along the length of the stent. As shown in FIG. 2, connectors struts 124*a* are parallel to the longitudinal axis of the stent whereas the angle of connector struts 124*b*, 124*c* etc. gradually increases relative to the longitudinal axis of the stent.

The connector struts of the stent of FIG. 2 may be characterized as being connected at one end to a first location on a serpentine circumferential band and at another end to a second location on an adjacent serpentine circumferential band. Desirably, the circumferential offset between turns which are connected to one another via a connector strut increases along the length of the stent. In the specific case of FIG. 2, the circumferential offset increases from no circumferential offset in the first connector column to the largest circumferential offset in the last connector column.

Figure 3:
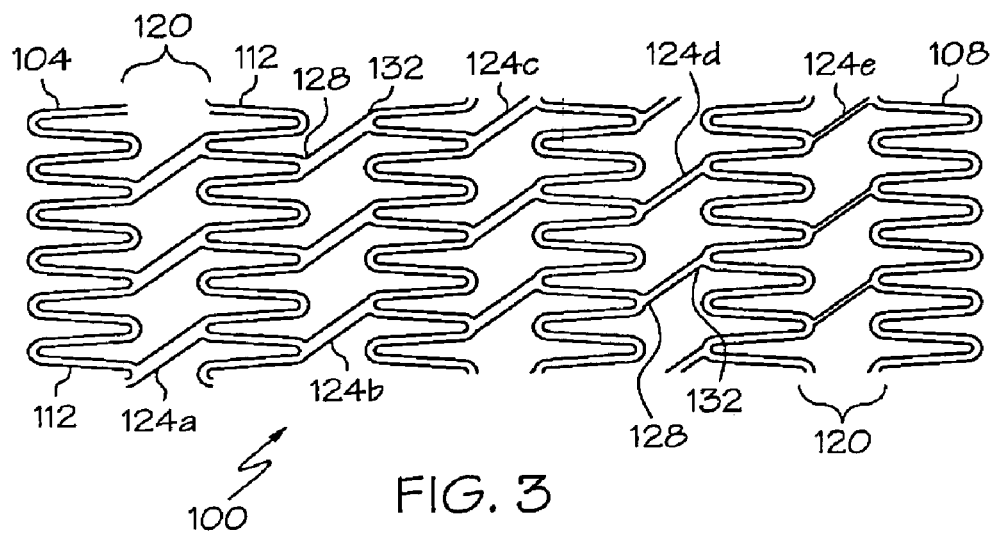

In one embodiment, the invention is directed to a stent such as that shown generally at 100 in FIG. 3, having a first free end 104 and a second free end 108, comprising a plurality of serpentine circumferential bands 112, and a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. The width of the connector struts 124 in a connector column decreases from the first free end of the stent to the second free end of the stent. As shown in FIG. 3, connector struts 124*a* are wider than connector struts 124*b* which are wider than connector struts 124*c* and so on, such that the width of the connector struts in a connector column decreases from one end of the stent to the other.

Desirably, the number of connectors per connector column is constant along the length of the stent. Also desirably, the length of the connector struts may be constant along the length of the stent.

Typically, as shown in FIG. 3, each connector strut is substantially straight and inclined at an angle of inclination relative to the longitudinal axis of the stent.

Figure 4A:
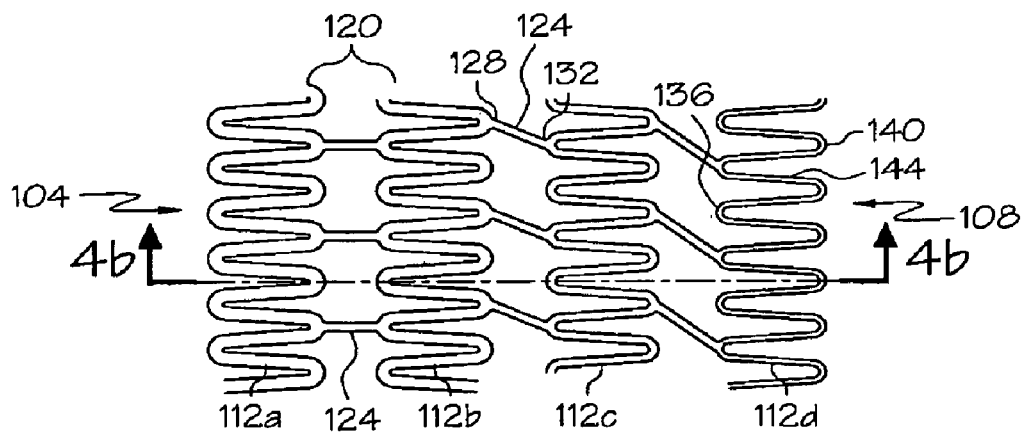
Figure 4B:
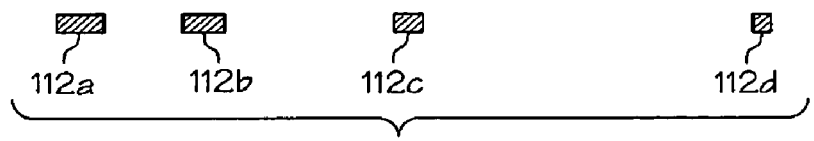
FIG. 4b shows a cross-section of a band strut in each band of the stent of FIG. 4a. The cross-section is taken in a direction perpendicular to the longitudinal axis of the stent.

The invention is also directed to a stent such as that shown generally at 100 in FIGS. 4*a* and 4*b*, having a first free end 104 and a second free end 108, comprising a plurality of serpentine circumferential bands 112, and a plurality of connector columns 120. Each serpentine band has a first end and a second end and characterized by a plurality of turns 136 at the first end and turns 140 at the second end. The turns are interconnected by band struts 144 having a width. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. Each connector strut is characterized by a width and connected at one end to one serpentine circumferential band and at another end to another serpentine circumferential band. The width of the band struts decreases from the first free end of the stent to the second free end of the stent. As shown in FIGS. 4*a* and 4*b*, the width of band struts 112*a* is greater than that of band struts 112*b* which is greater than that of band struts 112*c* and so on.

Desirably, the number of connectors per connector column is constant along the length of the stent. In the embodiment of FIG. 4*a*, the length of the connectors is not constant. It is also within the scope of the invention for the length of the connectors to be constant along the length of the stent.

Typically, each connector strut is substantially straight and inclined at an angle of inclination relative to the longitudinal axis of the stent.

Figure 5A:
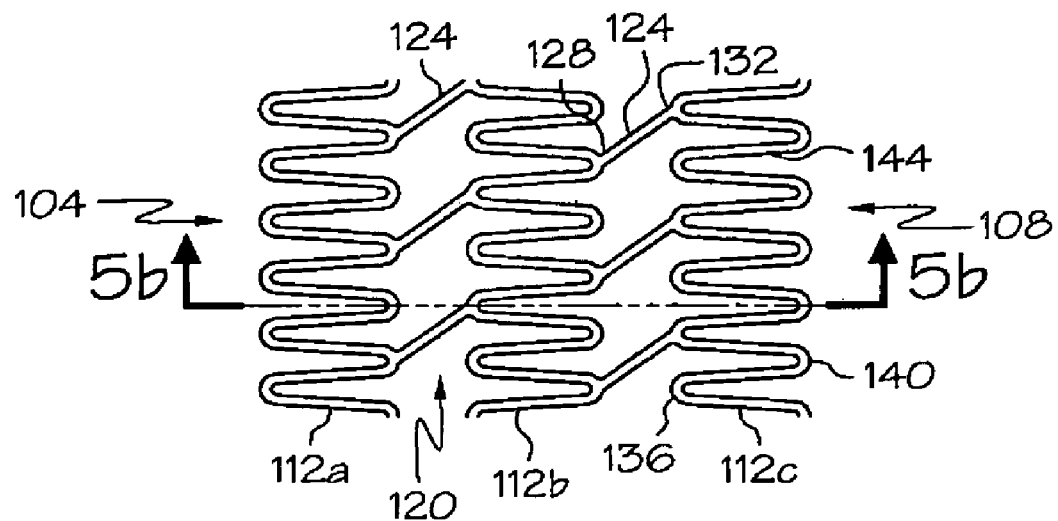
Figure 5B:
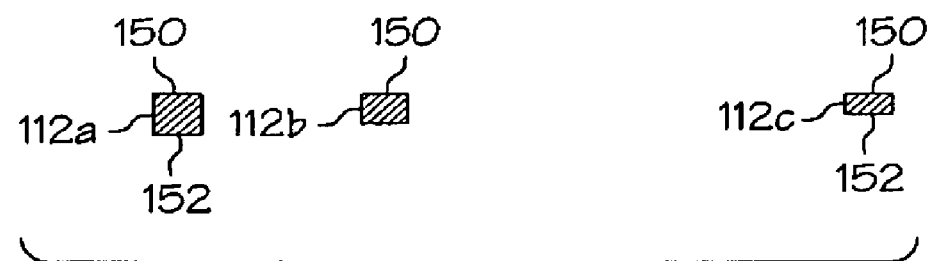
FIGS. 5b and 5c show cross-sectional views of band struts of embodiments of the stent depicted in FIG. 5a. The cross-section is taken in a direction perpendicular to the longitudinal axis of the stent.
Figure 5C:
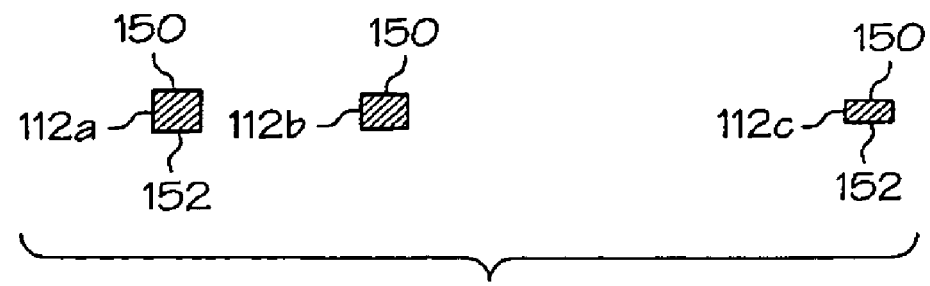

The invention is also directed to a stent such as that shown generally at 100 in FIGS. 5*a*–5*c*, having a first free end 104 and a second free end 108, and comprising a plurality of serpentine circumferential bands 112. Each serpentine circumferential band is characterized by a thickness. The stent further comprises a plurality of connector columns 120. Each serpentine band has a first end and a second end and characterized by a plurality of turns 136 at the first end and turns 140 at the second end. The turns are interconnected by band struts 144 having a width. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. The thickness of the serpentine circumferential bands decreases from the first free end of the stent to the second free end of the stent, as shown in FIGS. 5*b* and 5*c*. The outer surface of the stent is denoted by 150 in FIGS. 5*b* and 5*c*, and the inner surface is denoted by 152. The stent may be constructed so that the inner surface is smooth and the outer surfaces tapers, or so that the outer surface is smooth and the inner surface tapers, or so that both surfaces taper. The cross-section of each serpentine circumferential band may be rectangular, trapezoidal, or any other suitable shape. It should be noted that FIG. 5*b* depicts a stent having a smooth outer surface 150 and a taper along the inner surface 152, and the cross-sections shown are substantially rectangular. FIG. 5*c* depicts a stent having a continuous taper along both the outer surface 150 and inner surface 152, and the cross-sections shown are slightly trapezoidal.

Desirably, the number of connectors per connector column is constant along the length of the stent. Also desirably, the length of the connectors may be constant along the length of the stent.

Typically, each connector strut is substantially straight and inclined at an angle of inclination relative to the longitudinal axis of the stent.

In the embodiments discussed above, the connector struts are connected to peaks and troughs. The connector struts may extend from the center of a peak, from the side of a peak or from a region between a peak and a trough. The connectors struts may extend contralaterally or ipsilaterally as defined in U.S. Pat. No. 6,123,721, U.S. Pat. No. 6,235,053 and U.S. Pat. No. 6,200,334.

Figure 6:
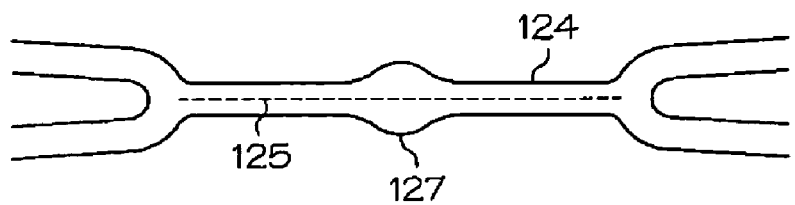
FIGS. 6–8 show various connector struts which may be used in the inventive stents.
Figure 7:
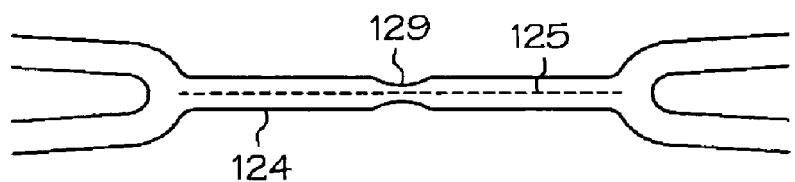
Figure 8:
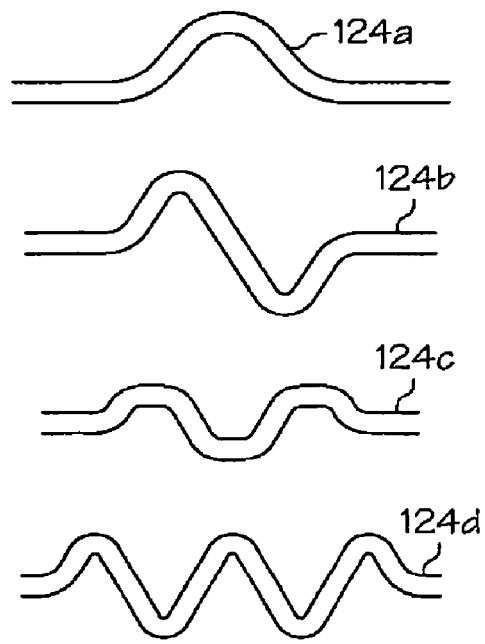

The connector struts shown in the figures discussed above are all substantially straight. The term 'substantially straight' refers to connectors struts which are straight to within manufacturing tolerances as well as to connector struts which have wider or narrower regions but which may be characterized as having a centerline, the entirety of which lies on the connector and which is straight. Examples of the latter are shown at 124 in FIGS. 6–8. Connector strut 124 in FIG. 6 includes a wider region 127. Centerline 125 (shown as a dotted line) is straight. Connector strut 124 in FIG. 7 includes a narrower region 129. Centerline 125 (shown as a dotted line) is straight.

It is also within the scope of the invention to use connector struts which are not substantially straight, for example connector struts that have at least one bend and optionally, at plurality of bends therein such that the connector strut may be characterized as comprising a plurality of portions at least some of which are non-parallel to one another. Non-limiting examples of such connector struts are shown at 124a–d in FIG. 8.

Figure 9:
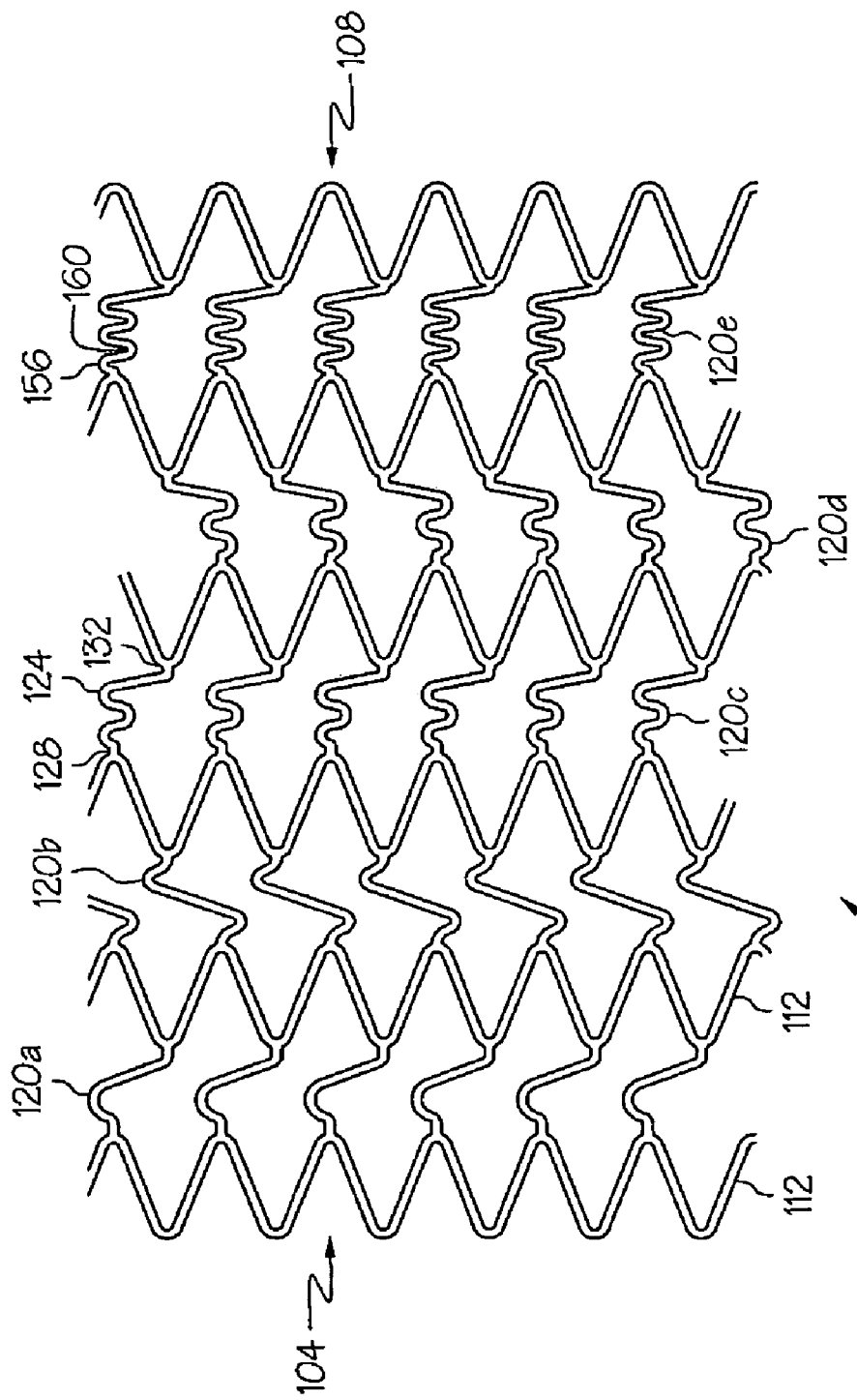
FIGS. 9–12 show flat patterns of further embodiments of inventive stents.

A further embodiment of the invention is shown generally at 100 in FIG. 9, having a first free end 104 and a second free end 108 and comprising a plurality of serpentine circumferential bands 112, and a plurality of connector columns 120. Each connector column is located between two adjacent circumferential bands 112, and comprises one or more connector struts 124. Each connector strut 124 is connected at one end 128 to one serpentine circumferential band and at another end 132 to another serpentine circumferential band. As shown in FIG. 9, the length of the connector struts 124 in a connector column may increase from the first free end 104 of the stent to the second free end 108 of the stent.

Further, each connector strut 124 may include one or more connector strut peaks 156 and one or more connector strut troughs 160. Generally, the overall length of a connector strut 124 increases as the number of peaks 156 and troughs 160 increases, although is it possible for separate connector struts 124 to have the same overall length while having differing numbers of peaks 156 and troughs 160.

In the embodiment shown in FIG. 9, connector column 120a is closest to the first free end 104 and includes connector struts 124 having only one full peak 156 and no full troughs 160. Connector column 120b includes connector struts 124 having one full peak 156 and one full trough 160. Desirably each subsequent connector column 120c–120e will include connector struts 124 having an additional peak or trough when compared to the previous connector column 120. Connector column 120e, as depicted, includes three full peaks 156 and two full troughs 160.

Alternatively, each connector strut 124 may be characterized as having one or more turns. In the embodiment shown in FIG. 9, the connector columns 120a–120e include connector struts 124 having an increasing number of turns when moving from the first free end 104 to the second free end 108.

Desirably, the number of connector struts 124 per connector column 120 remains constant along the length of the stent 100.

Figure 10:
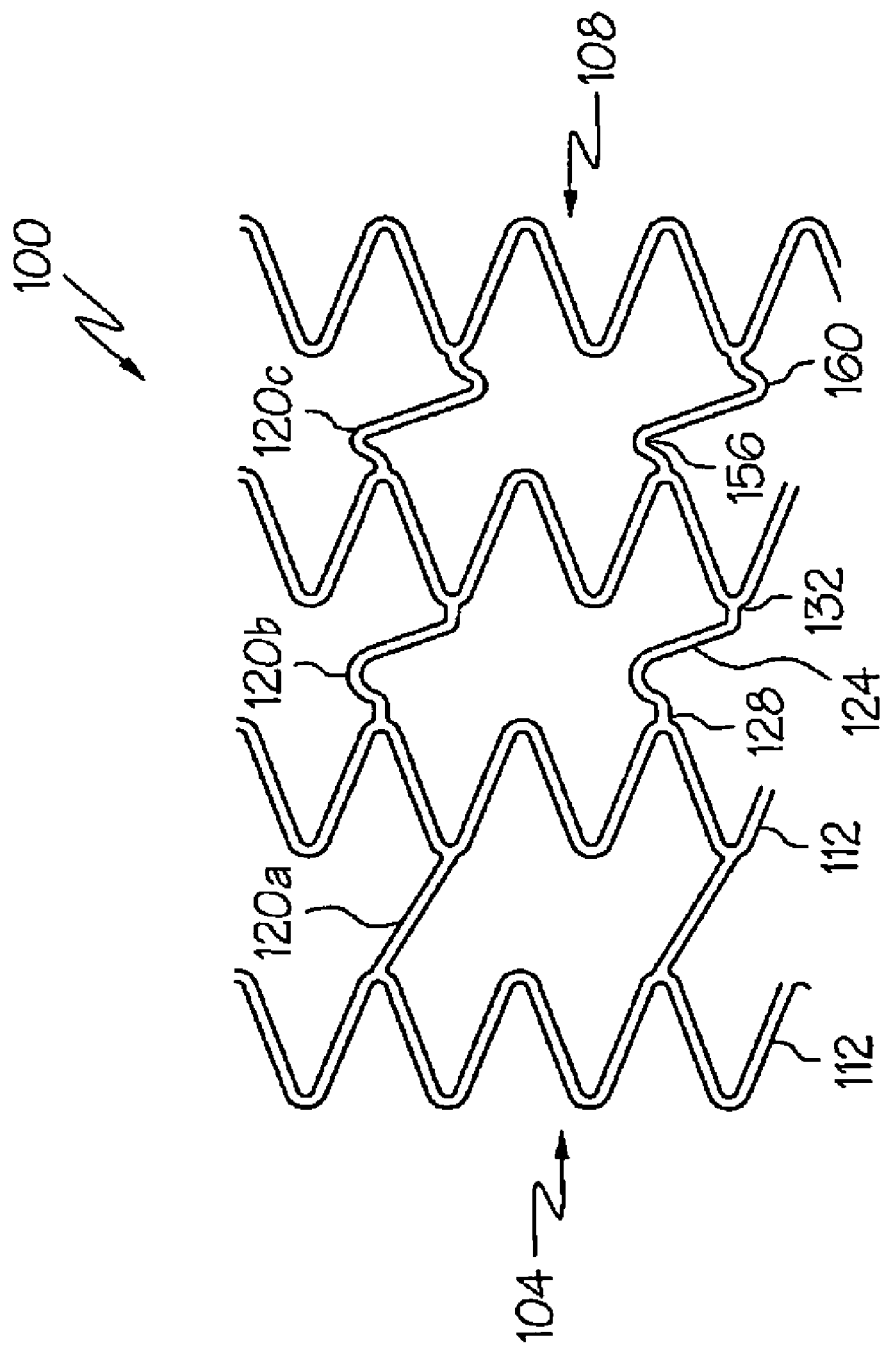

FIG. 10 depicts a similar embodiment of the invention having a first free end 104 and a second free end 108 and comprising a plurality of serpentine circumferential bands 112, and a plurality of connector columns 120. Each connector column is located between two adjacent circumferential bands 112, and comprises one or more connector struts 124. Each connector strut 124 is connected at one end 128 to one serpentine circumferential band and at another end 132 to another serpentine circumferential band.

In the embodiment of FIG. 10, the connector column 120a includes connector struts 124 that are substantially straight and non-parallel to the longitudinal axis of the stent. The connector struts 124 are inclined at an angle of inclination relative to the longitudinal axis of the stent 100. Alternatively the connector struts 124 of the connector column 120a may be characterized as including zero peaks 156 and zero troughs 160. The remaining connector columns 120 have an increasing number of turns. Generally, the length of a connector strut 124 increases as a higher number of peaks 156 and troughs 160 are included.

Figure 11:
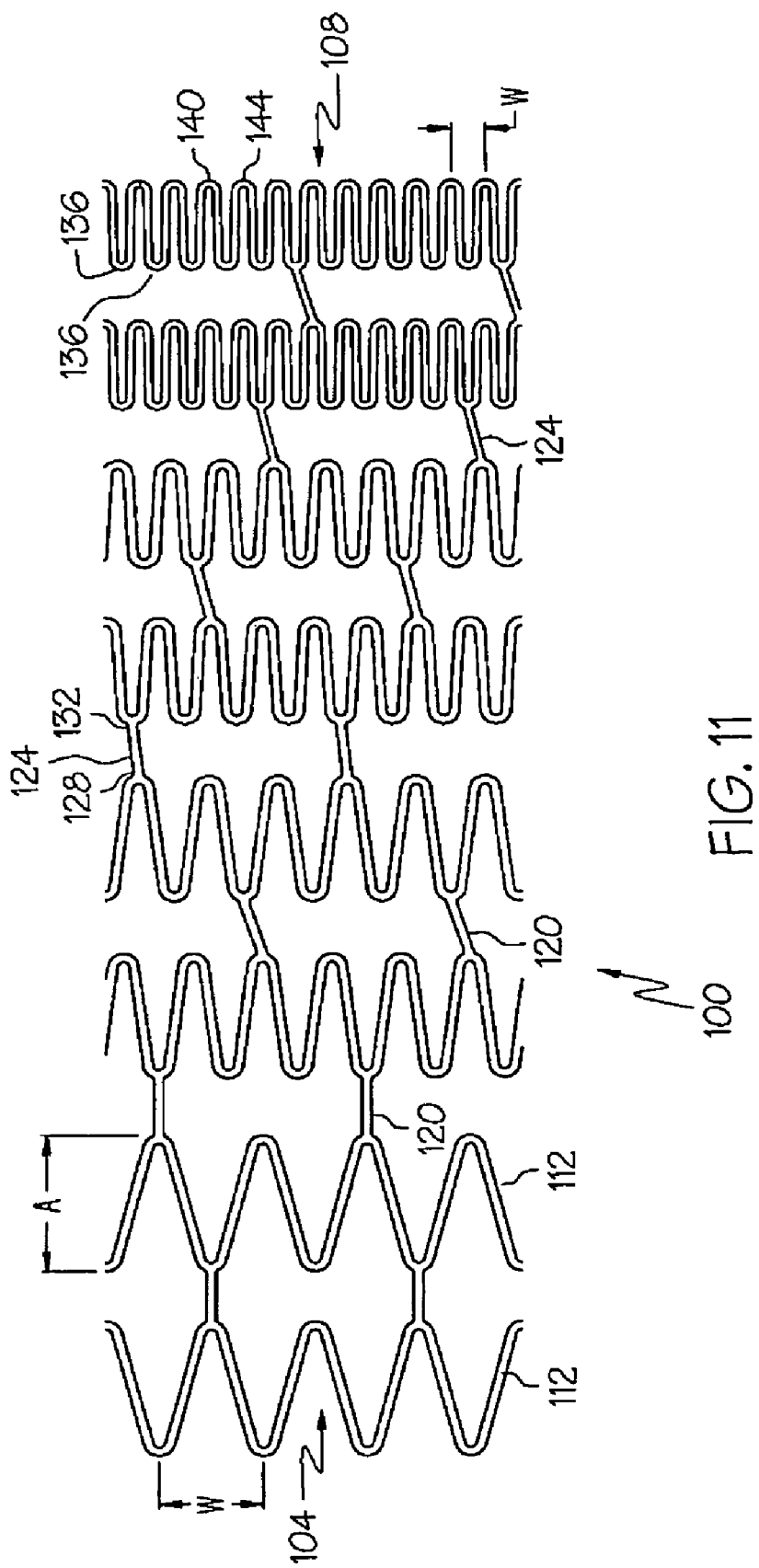

The invention is also directed to a stent such as that shown generally at 100 in FIG. 11, having a first free end 104 and a second free end 108, and comprising a plurality of serpentine circumferential bands 112. Each serpentine circumferential band may be characterized as having a plurality of sections, each section having a wavelength W and an amplitude A.

More generally, each serpentine circumferential band 112 may be characterized as having a first end and a second end and characterized by a plurality of turns 136 at the first end and turns 140 at the second end. The turns are interconnected by band struts 144.

Wavelength W of a serpentine circumferential band 112 section may be characterized as the distance from like points on a given serpentine circumferential band 112 in a direction perpendicular to the longitudinal axis of the stent, such as the distance from a given first end turn 136 to the next adjacent first end turn 136 of the serpentine circumferential band 112. Amplitude A of a serpentine circumferential band 112 section may be characterized as the distance from the serpentine circumferential band first end to the serpentine circumferential band second end.

The stent further comprises a plurality of connector columns 120. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band.

Desirably, the wavelength W of serpentine circumferential band 112 sections decreases from the first free end 104 of the stent to the second free end 108 of the stent, as shown in FIG. 11. Desirably, the amplitude A of serpentine circumferential band 112 sections decreases from the first free end 104 of the stent to the second free end 108 of the stent.

More generally, the serpentine circumferential bands 112 may be characterized as having an increasing number of turns from the first free end 104 of the stent to the second free end 108 of the stent. The serpentine circumferential bands 112 may also be characterized as having decreasing band strut 144 lengths from the first free end 104 to the second free end 108.

Typically each serpentine circumferential band 112 will have a constant wavelength W and amplitude A, although it is within the scope of the invention to have varying wavelength W and amplitude A within a given serpentine circumferential band 112.

Desirably, the number of connectors per connector column is constant along the length of the stent. Due to the change in wavelength W between adjacent serpentine circumferential bands 112, orientation of connector struts 124 is likely to change between adjacent connector columns 120 and between adjacent connector struts 124 within a given connector column 120. Typically, each connector strut 124 is substantially straight and inclined at an angle of inclination relative to the longitudinal axis of the stent.

The invention is also directed to a stent having greater flexibility at the proximal and distal ends when compared to a more rigid central portion. The increase in flexibility desirably allows the stent to be maneuvered through a bodily vessel more easily. Desirably there is an increase in bending flexibility about the stent longitudinal axis, and the increase in flexibility is fairly gradual from the central portion of the stent to either end. The increased flexibility may be accomplished by any of the methods disclosed herein, combinations of any of the methods or in any other suitable way. For example, connector columns 120 near the center of the stent may have more connector struts 124 than connector columns 120 located closer to the proximal or distal end. Connector struts 124 may alternatively or additionally increase in length and/or angle of inclination relative to the longitudinal axis of the stent from the center portion of the stent to the proximal and/or distal ends. Connector struts 124 may alternatively or additionally decrease in width, thickness or cross-sectional area from the center portion of the stent to the proximal or distal ends. The serpentine circumferential bands 112 may alternatively or additionally decrease in width, thickness or cross-sectional area from the center portion of the stent to the proximal or distal ends. Connector struts 124 may alternatively or additionally include one or more connector strut peaks 156 and one or more connector strut troughs 160, and the number of peaks 156 and troughs 160 may increase from the center portion of the stent to the proximal or distal ends. The serpentine circumferential bands 112 may alternatively or additionally increase in wavelength and/or amplitude from the center portion of the stent to the proximal or distal ends.

Figure 12:
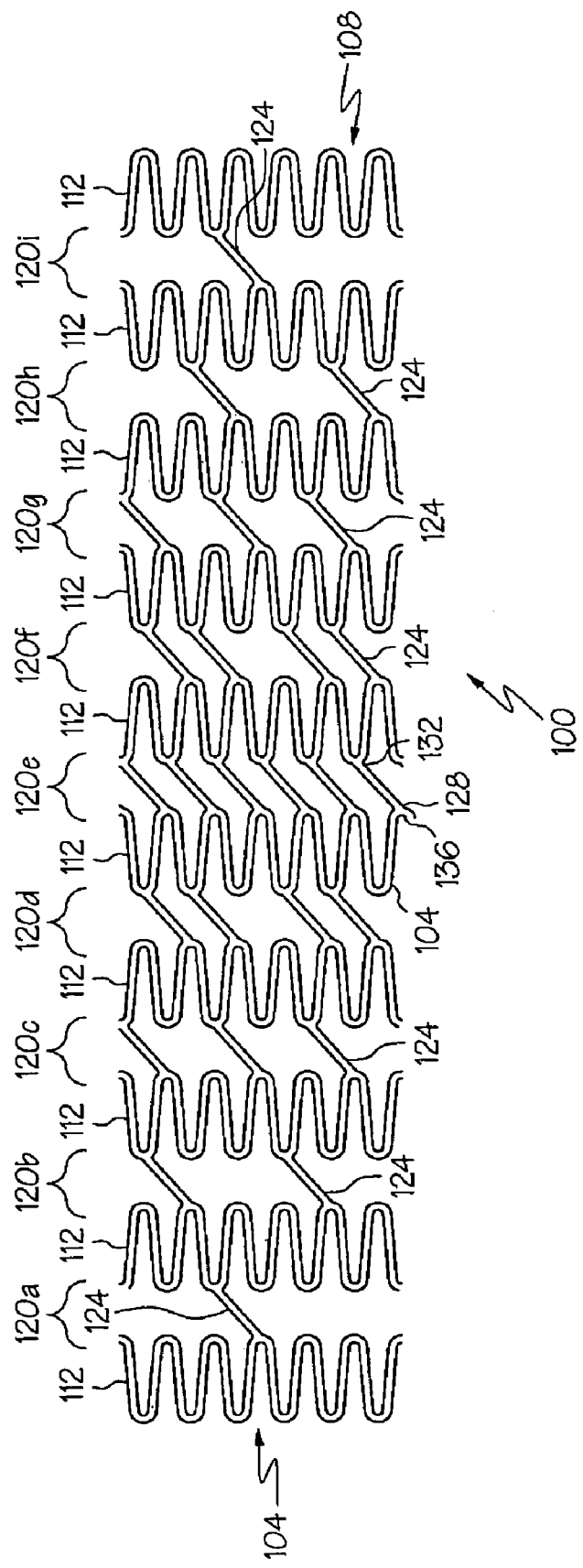

Referring to FIG. 12, a stent is depicted which has greater flexibility at the proximal and distal ends when compared to a more rigid central portion. The stent 100 includes a first free end 104 and a second free end 108, a plurality of serpentine circumferential bands 112, and a plurality of connector columns 120*a*–*i*. The stent further has a central longitudinal axis, and a midpoint located along the longitudinal axis equidistant from the first free end 104 and the second free end 108. Each connector column 120 is located between two adjacent serpentine circumferential bands 112 and comprises one or more connector struts 124. Each connector strut 124 is connected at one end 128 to one serpentine circumferential band and at another end 132 to another serpentine circumferential band. As shown in FIG. 12, the number of connectors per connector column decreases from the central portion of the stent to the proximal or distal ends.

Desirably, as shown in FIG. 12, the number of connectors per connector column decreases continuously from the central portion of the stent to the proximal or distal ends. The invention also contemplates embodiments in which the number of connectors decreases from the central portion to the proximal or distal ends, but not continuously, as, for example, would be the case if the third connector column 120*c* of the stent of FIG. 12 were modified to have the same number of connector struts as the second connector column 120*b*. Optionally, the number of connector struts 124 per column 120 may decrease uniformly.

The decrease in the number of connector struts 124 per connector column 120 results in a stent having an increasing flexibility at each end of the stent.

FIG. 13 shows an embodiment of a flat pattern of an inventive stent. The embodiment is similar to the embodiment shown in FIG. 1, while further comprising an additional connector 124 in connector column 124*a*.

Although specific embodiments of additional inventive stents having greater flexibility at the proximal and distal ends than at the central portion have not been depicted in the Figures, it should be understood that any method or combination of methods described herein for causing a change in flexibility may be utilized.

Suitable methods for manufacturing the inventive stents include laser cutting, chemical etching or stamping of a tube. The inventive stents may also be manufactured by laser cutting, chemically etching, stamping a flat sheet, rolling the sheet and welding the sheet, by electrode discharge machining, or by molding the stent with the desired design. The stent may also be manufactured by assembling a plurality of serpentine circumferential bands and welding or adhesively joining them to one another via connectors.

Achieving varying thicknesses of portions of the stent 100 according to various embodiments of the invention may be achieved in a variety of ways. Desirably, the base material used to form the stent includes a tapering thickness. Other methods include selective polishing or machining, applying an acid bath to a portion or portions of the stent, suitable chemical etching, or any other method of achieving the desired resulting thickness that is known in the art.

Any suitable stent material may be used in the manufacture of the inventive stents disclosed herein. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel titanium alloys generically known as "nitinol", platinum/tungsten alloys and titanium alloys. The invention also contemplates the use of more than one material in the inventive stents. For example, the first serpentine bands and the second serpentine bands may be made of different materials. Optionally, the connectors may be made of a different material than the first and/or second serpentine bands.

The inventive stents disclosed herein may be balloon-expandable, self-expanding or a hybrid of the two.

In the case of balloon-expandable stents, a balloon catheter may be used to deliver the stent to a desired bodily location. The balloon is then expanded, causing the stent to expand. The balloon may then be deflated and the catheter withdrawn. In the case of a self-expanding stent, the stent may be delivered on a catheter suited for delivery of self-expanding stents. Typically, such catheters include will include a retention sheath to maintain the stent in position until it is to be deployed. At the time of deployment, the sheath is withdrawn and the stent allowed to expand.

The invention is also directed to a stent-delivery catheter and any of the inventive stents disclosed herein. Details of stent-delivery catheters may be found in U.S. Pat. No. 6,120,522 and U.S. Pat. No. 6,506,201.

Desirably, in all of the embodiments disclosed above, first end 104 constitutes the proximal end of the stent when mounted on a catheter and second end 108 constitutes the distal end of the stent.

The inventive stents disclosed herein may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery.

The inventive medical devices may also be provided with various bio-compatible coatings to enhance various properties of the inventive medical devices. For example, the inventive medical devices may be provided with lubricious coatings or other polymeric coatings. An example of a suitable polymeric coating is PTFE.

The inventive stents may include one or more coatings which comprise one or more therapeutic agents, cellular materials, polymeric agents, or the like.

The therapeutic agent may be non-genetic or genetic. Suitable non-genetic therapeutic agents include anti-thrombogenic agents such as heparin, heparin derivatives, urokinase, and PPack (dextrophenylalanine proline arginine chloromethylketone), anti-proliferative agents such as enoxaprin, angiopeptin, or monoclonal antibodies capable of blocking smooth muscle cell proliferation, hirudin, and acetylsalicylic acid, anti-inflammatory agents such as dexamethasone, prednisolone, corticosterone, budesonide, estrogen, sulfasalazine, and mesalamine, antineoplastic/antiproliferative/anti-miotic agents such as paclitaxel, 5-fluorouracil, cisplatin, vinblastine, vincristine, epothilones, endostatin, angiostatin and thymidine kinase inhibitors, anesthetic agents such as lidocaine, bupivacaine, and ropivacaine, anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides, vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents; vasodilating agents; and agents which interfere with endogenous vasoactive mechanisms.

Suitable genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7 are particularly desirable. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Suitable cellular materials include cells of human origin (autologous or allogeneic) or from an animal source (xenogeneic), genetically engineered if desired to deliver proteins of interest at the transplant site. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAYHDROL®, etc.), fibrin, collagen and derivatives thereof, polysaccharides such as celluloses, starches, dextrans, alginates and derivatives, hyaluronic acid, squalene emulsions. Desirably, polyacrylic acid, available as HYDROPLUS® (Boston Scientific Corporation, Natick, Mass.), and described in U.S. Pat. No. 5,091,205, the disclosure of which is hereby incorporated herein by reference, may be used. Also desirably, the polymer may be a copolymer of polylactic acid and polycaprolactone. Other materials include selected medical-grade biodegradable materials such as PGA-TMC, Tyrosine-Derived Polycarbonates and arylates, polycaprolactone co butyl acrylate and other co polymers, Poly-L-lactic acid blends with DL-Lactic Acid, Poly(lactic acid-co-glycolic acid), polycaprolactone co PLA, polycaprolactone co butyl acrylate and other copolymers, Tyrosine-Derived Polycarbonates and arylate, poly amino acid, polyphosphazenes, polyiminocarbonates, polydimethyltrimethylcarbonates, biodegradable $CA/PO_4$'s, cyanoacrylate, 50/50 DLPLG, polydioxanone, polypropylene fumarate, or polydepsipeptides.

Other suitable coatings include macromolecules such as chitosan and Hydroxylpropylmethylcellulose. Surface erodible materials may also be used. Coatings may also comprise maleic anhydride copolymers, zinc-calcium phosphate and amorphous polyanhydrides.

The inventive stents may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

In addition to the specific embodiments claimed below, the invention is also directed to other embodiments having any other possible combination of the dependent features claimed below. As such, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1 or claim 2; claim 4 may be taken as alternatively dependent on any of claims 1–3; claim 5 may be taken as alternatively dependent on any of claims 1–4; etc.).

Those familiar with the art may recognize other equivalents to the specific embodiments described herein which equivalents are also intended to be encompassed by the claims attached hereto.

The invention claimed is:

1. A stent having a first free end and second free end, the stent comprising
a plurality of serpentine circumferential bands, and
a plurality of connector columns, each connector column located between two adjacent circumferential bands, each connector column comprising at least one connector strut, each connector strut connected at one end to one serpentine circumferential band and at another end to another serpentine circumferential band,
the number of connector struts per connector column decreasing uniformly from the first free end of the stent to the second free end of the stent.

2. The stent of claim 1 wherein one of the connector columns has only a single connector strut.

3. The stent of claim 2 wherein each connector strut is connected at one end to a first location on a serpentine circumferential band and at another end to a second location on an adjacent serpentine circumferential band, the second location longitudinally and circumferentially offset from the first location.

4. The stent of claim 1 wherein each connector strut is connected at one end to a first location on a serpentine circumferential band and at another end to a second location on an adjacent serpentine circumferential band, the second location longitudinally and circumferentially offset from the first location.

5. A stent having a first free end and a second free end, the stent comprising
a plurality of serpentine bands, and
a plurality of connector columns, a connector column located between each two adjacent serpentine bands, each connector column comprising at least one connector strut, each connector strut connected at one end to one serpentine band and at another end to another serpentine band,
wherein as the stent is traversed from the first free end to the second free end, each subsequent connector column includes less connector struts than any previous connector column.

6. The stent of claim 5 wherein each connector strut is connected at one end to a first location on a serpentine circumferential band and at another end to a second location on an adjacent serpentine circumferential band, the second location longitudinally and circumferentially offset from the first location.

7. The stent of claim 5 wherein the number of connector struts per connector column decreases uniformly from the first free end of the stent to the second free end of the stent.

8. The stent of claim 5 wherein one of the connector columns has only a single connector strut.

9. The stent of claim 5 wherein each serpentine band comprises a plurality of straight band struts connected by alternating peaks and troughs.

10. The stent of claim 9 wherein each connector strut is connected at one end to a first location on a serpentine circumferential band and at another end to a second location on an adjacent serpentine circumferential band, the second location longitudinally and circumferentially offset from the first location.

11. The stent of claim 5 wherein a first connector column located nearest the first free end includes more connector struts than any other connector column, and wherein a second connector column located nearest the second free end includes fewer connector struts than any other connector column.

12. A stent having a proximal end and a distal end, the stent comprising
a plurality of serpentine bands, and
a plurality of connector columns including a proximal most connector column and a distal most connector column, a connector column located between each two adjacent serpentine bands, each connector column comprising at least one connector strut, each connector strut connected at one end to one serpentine band and at another end to another serpentine band,
wherein a selected connector column includes more connector struts than other connector columns located distally to the selected connector column, and the selected connector column includes less connector struts than other connector columns located proximally to the selected connector column.

13. The stent of claim 12 wherein the distal most connector column has only a single connector strut.

14. The stent of claim 12 wherein each connector strut is connected at one end to a first location on a serpentine circumferential band and at another end to a second location on an adjacent serpentine circumferential band, the second location longitudinally and circumferentially offset from the first location.

15. The stent of claim 12 wherein the number of connector struts per connector column decreases uniformly from the proximal end of the stent to the distal end of the stent.

16. The stent of claim 12 wherein each serpentine band comprises a plurality of straight band struts connected by alternating peaks and troughs.

17. The stent of claim 12 wherein the proximal most connector column includes more connector struts than any other connector column, the distal most connector column includes fewer connector struts than any other connector column.

* * * * *